United States Patent [19]

Hennequin et al.

[11] Patent Number: 5,219,848
[45] Date of Patent: Jun. 15, 1993

[54] CEPHEM COMPOUNDS

[75] Inventors: Laurent F. A. Hennequin, Reims, France; David M. Hollinshead, Cheshire, England

[73] Assignees: ICI Pharma, Cergy Cedex, France; Imperial Chemical Industries PLC, London, England

[21] Appl. No.: 565,240

[22] Filed: Aug. 10, 1990

[30] Foreign Application Priority Data

Aug. 11, 1989 [EP] European Pat. Off. ........... 89402289

[51] Int. Cl.$^5$ ................. C07D 501/38; A61K 31/545
[52] U.S. Cl. ..................... 514/201; 514/202; 514/206; 540/221; 540/222; 540/225
[58] Field of Search ............. 540/221, 222, 225; 514/201, 202, 206

[56] References Cited

U.S. PATENT DOCUMENTS

| | | | |
|---|---|---|---|
| 4,278,733 | 7/1981 | Benzinger | 428/413 |
| 4,728,732 | 3/1988 | Skotnicki et al. | 540/227 |
| 4,728,734 | 3/1988 | Skotnicki et al. | 540/227 |
| 4,855,420 | 8/1989 | Jung | 540/222 |
| 4,939,250 | 7/1990 | Loftus et al. | 540/222 |
| 4,959,469 | 9/1990 | Nakagawa et al. | 540/222 |
| 5,017,569 | 5/1991 | Bertrandie | 514/206 |

FOREIGN PATENT DOCUMENTS 182210 5/1986 European Pat. Off. .
186187 7/1986 European Pat. Off. .
119885 3/1977 Japan .

*Primary Examiner*—Nicholas S. Rizzo
*Attorney, Agent, or Firm*—Cushman, Darby & Cushman

[57] ABSTRACT

Cephalosporin antibiotics having a 3-position substituent of the formula:

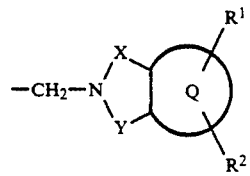

are described, wherein X is —CO—, —SO$_2$— or —COCH$_2$—; Y is —CO—, —SO$_2$— or —CH$_2$—; Q is a benzene, pyridine or naphthalene ring, R$^1$ and R$^2$ are ortho with respect to each other and are independently hydroxy or of the formula O—M wherein M is a moiety and the O—M bond is cleavable in vivo and ring Q may be further substituted by a variety of atoms and groups. Processes for their preparation and use are described.

10 Claims, No Drawings

CEPHEM COMPOUNDS

The present invention relates to cephalosporins and in particular to such compounds comprising a tertiary amine group. This invention further relates to processes for their preparation, to intermediates in their preparation, to their use as therapeutic agents and to pharmaceutical compositions containing them. The compounds of this invention are antibiotics and can be used in the treatment of any disease that is conventionally treated with antibiotics for example in the treatment of bacterial infection in mammals including humans. The compounds of this invention also have non-therapeutic uses as they can be used in conventional manner in industry for example they can be used as disinfectants and food preservatives. The compounds of this invention, however, are primarily of therapeutic interest as they show a desirable profile of activity and duration in their antibacterial effect.

Investigation into new cephalosporin derivatives has been intense over the past 25 years with many thousands of patents and scientific papers having been published. A particular problem associated with the commercially available cephalosporins is the lack of potency against strains of Pseudomonas.

A further problem associated with many commercially available cephalosporins is the lack of stability to β-lactamase enzyme producing organisms and the consequent loss of antibacterial activity.

The cephalosporin derivatives referred to herein are generally named in accordance with the 'cephem' nomenclature and numbering system proposed in J.A.C.S. 1962, 84,3400 and as depicted hereinbelow:

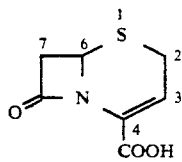

U.S. Pat. No. 4,728,732 discloses compounds of the formula:

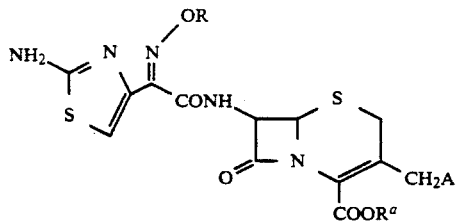

wherein
R is hydrogen, lower alkyl, lower alkenyl, lower alkynyl, cyclo lower alkyl, aryl of 6–12 carbon atoms, all the said foregoing groups being optionally substituted with carboxy, lower alkoxycarbonyl, phenoxycarbonyl, amino, mono- or di-lower alkyl substituted amino, hydroxy, lower alkoxy, phenoxy, carbamoyl, lower alkylcarbonyl, benzoyl, cyano, nitro, formamido, lower alkanoylamino or benzamido;
$R^a$ is hydrogen, lower alkyl or an alkali metal cation;
A is

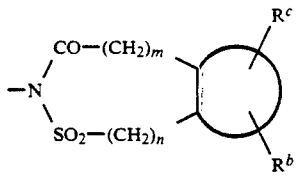

$R^b$ and $R^c$ are each individually lower alkyl, carboxy, lower alkoxycarbonyl, phenoxycarbonyl, amino, mono- or di-lower alkyl substituted amino, hydroxy, lower alkoxy, phenoxy, carbamoyl, mono- or di-lower alkyl substituted carbamoyl, lower alkylcarbonyl, benzoyl, cyano, nitro, lower alkanoylamino or benzamido;
$m = 0-1$;
$n = 0-1$;
B represents

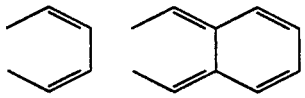

or a 5- or 6-membered unsaturated aza-, diaza-, triaza-, tetraza-, thia-, thiaza-, oxathia-, oxathiaza-, oxa-, dioxa-, oxaza- or oxadiazacyclic moiety; and the dotted line denotes an optional double bond.

We have now discovered a class of cephalosporin compounds, which partially overlap with U.S. Pat. No. 4,728,732, having novel 3-position substituents; these compounds possess very good antibacterial activity and in particular against strains of Pseudomonas.

In addition, the compounds of the present invention exhibit good stability to β-lactamase enzymes and thus are particularly useful in treating organisms that are β-lactamase producers.

Accordingly the present invention provides a cephalosporin compound having a 3-position substituent of the formula (I):

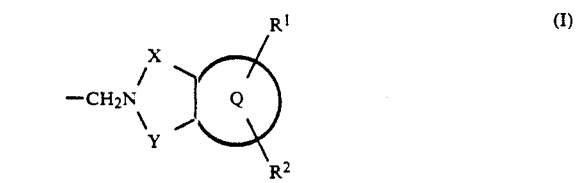

wherein:
X is —CO—, —SO$_2$— or —COCH$_2$— (wherein the carbonyl group is bonded to the nitrogen atom);
Y is —CO—, —SO$_2$— or —CH$_2$—;
Q is a benzene, pyridine or naphthalene ring system;
$R^1$ is hydroxy or a group of the formula O—M wherein M is a moiety and
the O—M bond is cleavable in vivo;
$R^2$ is ortho to $R^1$ and is hydroxy or a group of the formula O—M wherein
M is a moiety and the O—M bond is cleavable in vivo; and wherein Q is optionally substituted by $C_{1-6}$alkyl, halo, hydroxy, cyano, trifluoromethyl, nitro, amino, $C_{1-6}$alkylamino, di-$C_{1-6}$alkylamino, $C_{1-6}$alkanoyl, $C_{1-6}$alkoxy, $C_{1-6}$alkylthio, $C_{1-6}$alkanoyloxy, carbamoyl, $C_{1-6}$alkylcarbamoyl, di-$C_1$-

6alkylcarbamoyl, carboxy, carboxyC$_{1-6}$alkyl, C$_{1-6}$alkoxycarbonyl, hydroxyC$_{1-6}$alkyl, C$_{1-6}$alkanoylamino or C$_{1-6}$alkoxycarbonylC$_{1-6}$alkyl.

In a favoured aspect X is as defined hereinabove and Y is —CO— or —CH$_2$—. In one particular aspect X represents —COCH$_2$— and Y represents —CH$_2$—. In another particular aspect X represents —SO$_2$— and Y represents —CO—. In a particularly favoured aspect X and Y independently represent —CO—.

Q is a benzene, pyridine or naphthalene ring system. In said naphthalene ring system R$^1$ and R$^2$ may be located on either ring as may any optional substituents. Favourably Q is a benzene or pyridine ring; in particular Q is a benzene ring.

Favoured cephalosporin compounds of the present invention include those wherein Q is a benzene ring, Y is —CO— and X is —CO— or —SO$_2$—. Particularly preferred are those compounds wherein X is —CO—, in which case the cephalosporin 3-position substituent is a substituted phthalimidomethyl group:

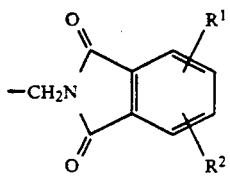

wherein the benzene ring may be optionally further substituted.

R$^1$ is hydroxy or a group of the formula O—M wherein M is a moiety and the O—M bond is cleavable in vivo. In a favoured aspect the O—M bond may be cleaved by hydrolysis. In a more favoured aspect the formula O—M represents an in vivo hydrolysable ester. In vivo hydrolysable esters are those pharmaceutically acceptable esters that hydrolyse in the human or animal body to produce the parent hydroxy compound. Such esters can be identified by administering, e.g. intravenously to a test animal, the compound under test and subsequently examining the test animal's body fluids. Suitable in vivo hydrolysable esters include C$_{1-6}$ alkanoyloxy for example acetoxy, propionyloxy, pivaloyloxy, C$_{1-4}$alkoxycarbonyloxy for example ethoxycarbonyloxy, phenylacetoxy and phthalidyl.

R$^2$ is hydroxy or a group of the formula O—M, wherein M is a moiety and the O—M bond is cleavable in vivo. Conveniently both R$^1$ and R$^2$ have the same value and are both hydroxy or are both groups of the formula O—M, wherein M is a moiety and the O—M bond is cleavable in vivo for example they are both in vivo hydrolysable esters such as acetoxy or pivaloyloxy.

As stated hereinbefore ring Q may be optionally substituted (on either ring in the case of naphthalene). Particular substituents are C$_{1-6}$alkyl for example methyl or ethyl; halo for example chloro, fluoro or bromo; hydroxy; hydroxyC$_{1-6}$alkyl for example hydroxymethyl; amino, nitro; cyano; C$_{1-6}$alkylamino for example methylamino or ethylamino; di-C$_{1-6}$alkylamino for example dimethylamino or diethylamino; C$_{1-6}$alkoxy for example methoxy or ethoxy; carboxy C$_{1-6}$alkyl for example carboxymethyl or carboxyethyl; C$_{1-6}$alkanoylamino for example acetamido; C$_{1-6}$alkanoyloxy for example acetoxy; C$_{1-6}$alkoxycarbonylC$_{1-6}$alkyl for example methoxycarbonylmethyl; trifluoromethyl; carboxy; C$_{1-6}$alkoxycarbonyl for example methoxycarbonyl or ethoxycarbonyl; carbamoyl; C$_{1-6}$alkylcarbamoyl for example methylcarbamoyl or ethylcarbamoyl; di-C$_{1-6}$alkylcarbamoyl for example dimethylcarbamoyl or diethylcarbamoyl; C$_{1-6}$alkanoyl for example acetyl; and C$_{1-6}$alkylthio for example methylthio or ethylthio.

Preferred substituents are bromo, chloro, carboxy, carboxymethyl and hydroxy.

As stated hereinbefore the present invention relates to cephalosporins having a novel 3-position substituent. A particular class of cephalosporins within the present invention is that of the formula (II):

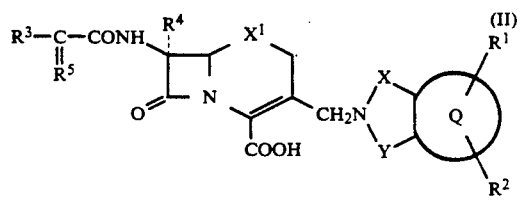

and salts and esters thereof wherein R$^1$, R$^2$, X, Y, and Q are as hereinbefore defined;

X$^1$ is sulphur, oxygen, methylene or sulphinyl;

R$^4$ is hydrogen, methoxy or formamido; and

R$^3$ and R$^5$ are groups known for such positions in the cephalosporin art.

Preferably X$^1$ is sulphur.

Preferably R$^4$ is hydrogen.

R$^3$ is for example 2-aminothiazol-4-yl or 2-aminooxazol-4-yl each optionally substituted in the 5-position by fluorine, chlorine or bromine, or R$^3$ is 5-aminoisothiazol-3-yl, 5-amino-1,2,4-thiadiazol-3-yl, 3-aminopyrazol-5-yl, 3-aminopyrazol-4-yl, 2-aminopyrimidin-5-yl, 2-aminopyrid-6-yl, 4-aminopyrimidin-2-yl, 2-amino-1,3,4-thiadiazol-5-yl or 5-amino-1-methyl-1,2,4-triazol-3-yl;

R$^5$ is for example of the formula =N.O.R$^6$ (having the syn configuration about the double bond) wherein R$^6$ is hydrogen (1-6C)alkyl, (3-8C)cycloalkyl, (1-3C)alkyl(3-6C)cycloalkyl, (3-6C)cycloalkyl(1-3C)alkyl, (3-6C)alkenyl, optionally substituted by carboxy, (5-8C)cycloalkenyl, (3-6C)alkynyl, (2-5C)alkylcarbamoyl, phenylcarbamoyl, benzylcarbamoyl, (1-4C)alkylcarbamoyl(1-4C)alkyl, di(1-4C)alkylcarbamoyl(1-4C)alkyl, (1-4C)haloalkylcarbamoyl(1-4C)alkyl, (1-3C)haloalkyl, (2-6C)hydroxyalkyl, (1-4C)alkoxy(2-4C)alkyl, (1-4C)alkylthio(2-4C)alkyl, (1-4C)alkanesulphinyl(1-4C)alkyl, (1-4C)alkanesulphonyl(1-4C)alkyl, (2-6C)aminoalkyl, (1-4C)alkylamino(1-6C)alkyl, (2-8C)dialkylamino(2-6C)alkyl, (1-5C)cyanoalkyl, 3-amino-3-carboxypropyl, 2-(amidinothio)ethyl, 2-(N-aminoamidinothio)ethyl, tetrahydropyran-2-yl, thietan-3-yl, 2-oxopyrrolidinyl, or 2-oxotetrahydrofuranyl, or R$^6$ is of the formula (III):

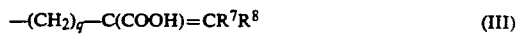

wherein q is one or two and R$^7$ and R$^8$ are independently hydrogen or C$_{1-4}$alkyl; or R$^6$ is of the formula (IV):

wherein r is 0–3, R$^9$ is hydrogen, (1-3C)alkyl or methylthio, R$^{10}$ is hydrogen, (1-3C)alkyl, (3-7C)cycloalkyl, cyano, carboxy, (2-5C)carboxyalkyl or methanesulphonylamino, or $R^9$ and $R^{10}$ are joined to form, together with the carbon to which they are attached, a (3-7C-)carbocyclic ring, and $R^{11}$ is hydroxy, amino, (1-4C)alkoxy, (1-4C) alkylamino or of the formula $NHOR^{12}$ in which $R^{12}$ is hydrogen or (1-4C)alkyl;

or $R^5$ may be of the formula $=CH.R^{13}$ wherein $R^{13}$ is hydrogen, halogen, (1-6C)alkyl, (3-7C)cycloalkyl, (2-6C)alkenyl, (3-7C)cycloalkenyl, phenyl or benzyl.

Particular meaning for $R^6$ are hydrogen, methyl, ethyl, isopropyl, t-butyl, cyclopropyl, cyclobutyl, cyclopentyl, cyclohexyl, methylcyclopropyl, methylcyclobutyl, methylcyclopentyl, methylcyclohexyl, cyclopropylmethyl, cyclobutylmethyl, cyclopentylmethyl, allyl, cyclopentenyl, cyclohexenyl, propargyl, methylcarbamoyl, ethylcarbamoyl, phenylcarbamoyl, benzylcarbamoyl, 2-chloroethyl, 2-fluoroethyl, 2-bromoethyl, 2-hydroxyethyl, 3-hydroxypropyl, 2-methoxyethyl, 2-ethoxyethyl, 2-methylthio-ethyl, 2-methanesulphinylethyl, 2-methanesulphonyl-ethyl, 2-aminoethyl, 3-aminopropyl, 2-methylamino ethyl, 2-dimethylaminoethyl, cyanomethyl, 2-cyanoethyl, azidomethyl, 2-azidoethyl, ureidomethyl, 3-amino-3-carboxypropyl, 2-(amidino)ethyl, 2-(N-aminoamidino)-ethyl, tetrahydropyran-2-yl, thietan-3-yl, 2-oxopyrrolidinyl and 2-oxo-tetrahydrofuran-3-yl, or, when $R^6$ is of the formula (III) in which q is 1 or 2, a particular meaning for $R^6$ is when $R^7$ and $R^8$ are hydrogen or methyl, or, when $R^6$ is of the formula (IV), a particular meaning for $R^6$ is when $r=0$ and $R^9$ is hydrogen, methyl or methylthio, $R^{10}$ is hydrogen, methyl, cyclopropyl, cyclobutyl, cyclopentyl, cyclohexyl, cyano, carboxy, carboxymethyl, 2-carboxyethyl or methanesulphonylamino, or when $R^9$ and $R^{10}$ are joined to form, together with the carbon to which they are attached, a cyclopropane, cyclobutane, cyclopentane, cyclohexane or cycloheptane ring and $R^{11}$ is hydroxy, amino, methoxy, ethoxy, methylamino, ethylamino, or of the formula $NHOR^{12}$ in which $R^{12}$ is hydrogen, methyl or ethyl.

Preferably $R^6$ is $C_{1-6}$alkyl for example methyl or ethyl, 1-carboxycyclobutyl, 1-carboxycyclopentyl, or 2-carboxyprop-2-yl. In particular $R^6$ is 2-carboxyprop-2-yl.

Particular meanings for $R^{13}$ are hydrogen, methyl, ethyl or chlorine.

It should be realised that the present invention covers all tautomeric forms, for example when Q represents a pyridine ring and $R^1$ and $R^2$ are both hydroxy the 3-position substituent may be depicted as:

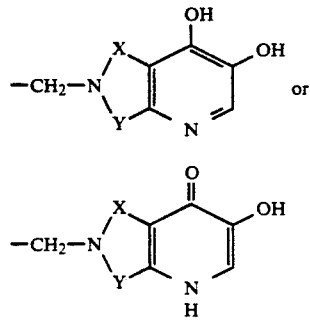

Such tautomers are within the scope of the present invention.

As stated hereinbefore the compounds of this invention are primarily intended for use in therapy. Therefore in a preferred aspect the present invention provides a cephalosporin compound having a 3-position substituent of the formula I or a pharmaceutically acceptable salt or ester thereof. Suitable salts include acid addition salts such as hydrochloride, hydrobromide, citrate, maleate and salts formed with phosphoric and sulphuric acid. In another aspect suitable salts are base salts such as an alkali metal salt for example sodium or potassium, an alkaline earth metal salt for example calcium or magnesium, an organic amine salt for example triethylamine, morpholine, N-methylpiperidine, N-ethylpiperidine, procaine, dibenzylamine or N,N-dibenzylethylamine.

In order to use a compound of the present invention or a pharmaceutically acceptable salt or ester thereof for the therapeutic treatment of mammals including humans, in particular in treating infection, it is normally formulated in accordance with standard pharmaceutical practice as a pharmaceutical composition.

Therefore in another aspect the present invention provides a pharmaceutical composition which comprises a cephalosporin compound having a 3-position substituent of the formula I or a pharmaceutically acceptable salt or ester thereof and a pharmaceutically acceptable carrier.

The pharmaceutical compositions of this invention may be administered in standard manner for the disease condition that it is desired to treat, for example by oral, rectal or parenteral administration. For these purposes it may be formulated by means known to the art into the form of, for example, tablets, capsules, aqueous or oily solutions or suspensions, emulsions, dispersible powders, suppositories and sterile injectable aqueous or oily solutions or suspensions.

In addition to the pharmaceutically acceptable cephalosporin derivative of the present invention the pharmaceutical composition of the invention may also contain, or be co-administered with, one or more known drugs selected from other clinically useful antibacterial agents (for example other beta-lactams or aminoglycosides), inhibitors of beta-lactamase (for example clavulanic acid), renal tubular blocking agents (e.g. probenicid) and inhibitors of metabolising enzymes (for example inhibitors of peptidases, for example Z-2-acylamino-3-substituted propenoates).

A preferred pharmaceutical composition of the invention is one suitable for intravenous, subcutaneous or intramuscular injection, for example a sterile injectable containing between 1 and 50% w/w of the cephalosporin derivative, or one suitable for oral administration in unit dosage form, for example a tablet or capsule which contains between 100 mg. and 1 g. of the cephalosporin derivative.

The pharmaceutical compositions of the invention will normally be administered to man in order to combat infections caused by bacteria, in the same general manner as that employed for cephalothin, cefoxitin, cephradine, ceftazidime and other known clinically used cephalosporin derivatives, due allowance being made in terms of dose levels for the potency of the cephalosporin derivative of the present invention relative to the known clinically used cephalosporins. Thus each patient will receive a daily intravenous, subcutaneous or intramuscular dose of 0.05 to 30 g., and preferably 0.1 to 10 g., of the cephalosporin derivative, the composition being administered 1 to 4 times per day, preferably 1 or 2 times a day. The intravenous, subcutaneous and intramuscular dose may be given by means of a bolus injection. Alternatively the intravenous dose may be given by continuous infusion over a period of time. Alternatively each patient will receive a daily oral dose which is approximately equivalent to the daily parenteral dose. Thus a preferred daily oral dose is 0.5 to 10 g. of the cephalosporin derivative, the composition being administered 1 to 4 times per day.

In a further aspect the present invention provides a process for preparing a cephalosporin compound having a 3-position substituent of the formula I, which process comprises:

a) deprotecting a cephalosporin compound having a 3-position substituent of the formula (V):

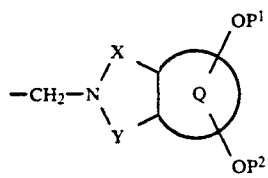

wherein $P^1$ and $P^2$ are independently hydrogen or hydroxy protecting groups which may optionally be joined to form a ring and at least one of $P^1$ and $P^2$ is a hydroxy protecting group;

b) for preparing compounds wherein X is —CO— or —COCH$_2$— and Y is —CO— or —CH$_2$—, cyclizing a cephalosporin compound having a 3-position substituent of the formula (VI):

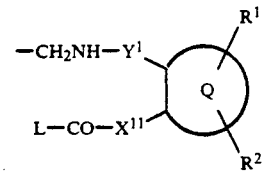

wherein L is a leaving group, $X^{11}$ is a bond or —CH$_2$— and $Y^1$ is —CO— or —CH$_2$—; or c) for preparing compounds wherein at least one of X and Y is —SO$_2$—, reacting a cephalosporin compound having a 3-position substituent of the formula: —CH$_2$I with a compound of the formula (VII):

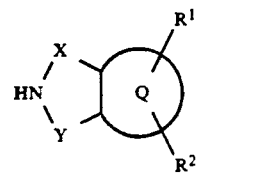

d) for preparing compounds of the formula (II), reacting a compound of the formula (VIII) with a compound of the formula (IX) or a reactive derivative thereof:

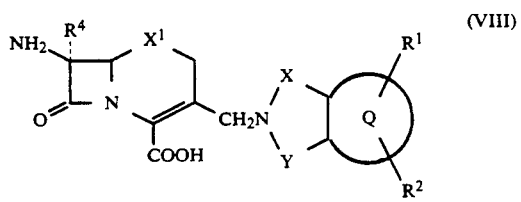

or e) for preparing compounds of the formula (II) wherein $R^5$ is a group =NOR$^6$, reacting a compound of the formula (X):

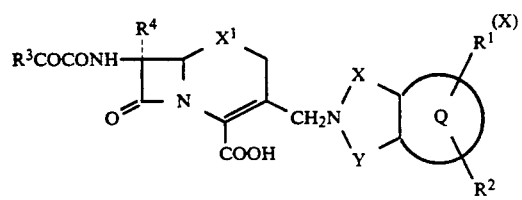

with a compound of the formula: R$^6$ONH$_2$; or f) for preparing compounds of the formula (II) wherein $R^5$ is a group =NOR$^6$ and R$^6$ is other than hydrogen, reacting a compound of the formula (II) wherein $R^5$ is a group =NOH with a compound of the formula (XI):

wherein $L^1$ is a leaving group and $R^{14}$ is a group $R^6$ other than hydrogen; or g) for preparing compounds of the formula (II) forming a group $R^3$ by cyclizing an appropriate precursor thereof:

wherein any functional groups are optionally protected: and thereafter, if necessary:

i) removing any protecting group,
ii) converting a hydroxy group to a group —O—M,
iii) converting compounds wherein $X^1$ is S to compounds wherein $X^1$ is sulphinyl and vice versa,
iv) forming a pharmaceutically acceptable salt.

In the process of this invention any functional group can be optionally protected, if appropriate. Such protecting groups may in general be chosen from any of the groups described in the literature or known to the skilled chemist as appropriate for the protection of the group in question, and may be introduced by conventional methods.

Protecting groups may be removed by any convenient method as described in the literature or known to the skilled chemist as appropriate for the removal of the protecting group in question, such methods being chosen so as to effect removal of the protecting group with minimum disturbance of groups elsewhere in the molecule.

Examples of hydroxy protecting groups, in particular groups $P^1$ and $P^2$, include alkanoyl groups (e.g. acetyl); alkoxycarbonyl groups (e.g. t-butoxycarbonyl); haloalkoxycarbonyl groups (e.g. 2-iodoethoxycarbonyl, 2,2,2-trichloroethoxycarbonyl); arylalkoxycarbonyl groups (e.g. benzoyloxycarbonyl, p-methoxybenzyloxycarbonyl, o-nitrobenzyloxycarbonyl, p-nitrobenzyloxycarbonyl); trialkylsilyl (e.g. trimethylsilyl, t-butyldimethylsilyl) and arylalkyl (e.g. benzyl) groups. The two hydroxy groups substituted on adjacent carbon atoms, for example —OP$^1$ and —OP$^2$, may be protected in the form of a cyclic acetal such as the methylenedioxy or o-phenylenedioxy moiety.

A carboxyl protecting group may be the residue of an ester-forming aliphatic or araliphatic alcohol or of an ester-forming phenol, silanol or stannanol (the said alcohol, phenol, silanol or stannanol preferably containing 1-20 carbon atoms).

Examples of carboxyl protecting groups include straight or branched chain (1-12C) alkyl groups (e.g. isopropyl, t-butyl); haloalkyl groups (e.g. 2-iodoethyl, 2,2,2-trichloroethyl); alkoxyalkyl groups (e.g. methoxymethyl, ethoxymethyl, isobutoxymethyl); alkanoyloxy alkyl groups, (e.g. acetoxymethyl, propionyloxymethyl, butyryloxymethyl, pivaloyloxymethyl); alkoxycarbonyloxyalkyl groups (e.g. 1-methoxycarbonyloxyethyl, 1-ethoxycarbonyloxyethyl); arylalkyl groups (e.g. p-methoxybenzyl, o-nitrobenzyl, p-nitrobenzyl, benzhydryl and phthalidyl); trialkylsilyl groups (e.g. trimethylsilyl and t-butyldimethylsilyl); trialkylsilylalkyl groups (e.g. trimethylsilylethyl); and (2-6C)alkenyl groups (e.g. allyl and vinylethyl).

Methods particularly appropriate for the removal of carboxyl protecting groups include for example acid-, base-, metal- or enzymically-catalysed hydrolysis.

Examples of amino protecting groups include formyl, aralkyl groups (e.g. benzyl and substituted benzyl, e.g. p-methoxybenzyl, nitrobenzyl and 2,4-dimethoxybenzyl, and triphenylmethyl); di-p-anisylmethyl and furylmethyl groups; acyl (e.g. alkoxycarbonyl and aralkoxycarbonyl e.g. t-butoxycarbonyl and benzyloxycarbonyl); trialkylsilyl (e.g. trimethylsilyl and t-butyldimethylsilyl); alkylidene (e.g. methylidene); benzylidene and substituted benzylidene groups; and the phthalimido group.

In the above discussion of protecting groups, alkyl means $C_{1-4}$alkyl.

The cephalosporin compounds having a 3-position substituent of the formula (V) are prepared by methods analogous to those described for the preparation of cephalosporin compounds having a 3-position substituent of the formula (I).

The cyclisation of a cephalosporin compound having a 3-position substituent of the formula (VI) is typically performed at a non-extreme temperature, for example between 0° and 60° C., conveniently at ambient temperature. The cyclisation is generally performed in the presence of a base, such as an organic amine for example triethylamine, in a substantially inert organic solvent such as a polar aprotic solvent for example dimethylsulphoxide.

The cephalosporin compound having a 3-position substituent of the formula (VI) may be prepared and either isolated or reacted in situ.

Cephalosporin compounds having a 3-position substituent of the formula (VI) wherein Y is —CO— are conveniently formed in situ from the reaction of a 3-aminomethyl cephalosporin with a compound of the formula (XII):

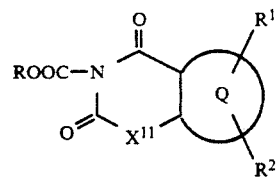

wherein $X^{11}$, $R^1$, $R^2$ and Q are as hereinbefore defined and R is typically $C_{1-6}$alkyl for example methyl or ethyl. This reaction is typically performed at a non-extreme temperature, for example between 0° and 60° C., in the presence of a base such as an organic amine for example triethylamine, in a substantially inert organic solvent for example dimethylsulphoxide. The reaction provides a cephalosporin having a 3-position substituent of the formula (VI) wherein L is ROOC—NH—, that is the leaving group is a urethane, for example R is $C_{1-6}$alkyl.

3-Aminomethyl cephalosporins are known in the art or are made by methods analogous thereto. See for example EP-A-127992 and EP-A-164944.

The compounds of the formula (XII) are prepared by the general methods of organic chemistry as known to those skilled in the art.

Cephalosporin compounds having a 3-position substituent of the formula (VI) wherein Y is —CH$_2$— are conveniently prepared by the reaction of a 3-aminomethyl cephalosporin with a compound of the formula (XIII):

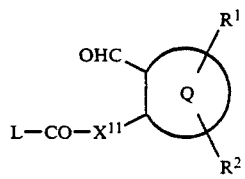

wherein L, $X^{11}$, Q, $R^1$ and $R^2$ are as hereinbefore defined, in a process of reductive amination. The reaction is typically performed at a non-extreme temperature, for example between 0° and 60° C., conveniently between 0° C. and ambient temperature. Suitable reducing agents include sodium borohydride and sodium cyanoborohydride.

The compounds of the formula (VI) may be prepared by the general methods of EP-A-267733 and EP-A-269298.

The reaction between a cephalosporin compound having a 3-position substituent of the formula —CH$_2$I and a compound of the formula (VII), wherein at least one of X and Y is —SO$_2$— is conveniently performed at a non-extreme temperature such as 0° to 60° C., for example at ambient temperature such as 0° to 60° C., for example at ambient temperature in a substantially inert organic solvent such as a polar aprotic solvent for example dimethylformamide or dimethylsulphoxide. The process is conveniently carried out in the presence of a base, for example an inorganic base such as a carbonate, or an alkali metal hydride (for example sodium hydride). The process may be performed by pre-reacting the compound of the formula (VII) with a suitable base to form the corresponding salt which is then reacted with the 3-iodomethyl cephalosporin.

3-Iodomethyl cephalosporins may be prepared by a method similar to that described by Bonjouklian et al., Tetrahedron Letters, 22, 3915 (1981). The compounds of the formula (VII) may be prepared by methods known in the art, for example certain compounds are described in U.S. Pat. No. 4,728,732.

The reaction between the compounds of the formulae (VIII) and (IX) is performed under conditions conventional in the cephalosporin art, for example under standard acylation conditions wherein for example the acid is activated as an acid bromide, acid chloride, anhydride or activated ester, or the reaction is performed in the presence of a coupling reagent such as dicyclohexylcarbodimide.

The compounds of the formula (VIII) can be prepared in a manner analogous to that described for the compounds having the 3-substituent of the formula (I), with the 7-amino group being optionally protected.

The reaction between compounds of the formula (X) and $R^6ONH_2$ is performed under conditions standard in the general chemical and/or cephalosporin art. The compounds of the formula (X) can be prepared in a manner analogous to that described for the compounds having the 3-substituent of the formula (I).

The reaction between the compound of the formula (II) wherein $R^5$ is a group $=NOH$ and a compound of the formula (XI) is performed under conditions standard in the general chemical and/or cephalosporin art.

A group $R^3$ may be formed by cyclizing an appropriate precursor. For example compounds of the formulae (XII) and (XIII):

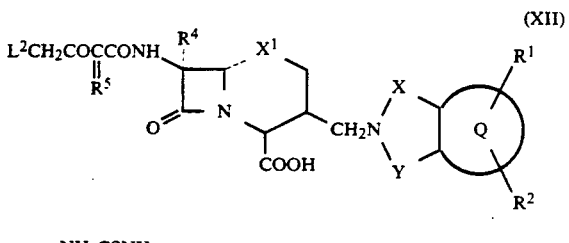

(XII)

$NH_2CSNH_2$  (XIII)

wherein $X^1$, $R^1$-$R^5$, X and Y are as hereinbefore defined and $L^2$ is a leaving group, may be reacted to form a 2-aminothiazol-4-yl group. A nitrogen atom of the thiourea may be optionally protected during this cyclization.

The compounds of the formula (XII) can be prepared in a manner analogous to that described for the compounds of the formula (I).

The compounds of the formulae (IX), (XI) and $R^6ONH_2$ are known from, or can be made by the methods of, the general chemical and/or cephalosporin art.

The compounds of the formulae (VIII), (X) and (XII) are novel and as such form a further aspect of the present invention.

The following biological test methods, data and Examples serve to illustrate this invention.

Antibacterial Activity

The pharmaceutically acceptable cephalosporin compounds of the present invention are useful antibacterial agents having a broad spectrum of activity in vitro against standard laboratory microorganisms, both Gram-negative and Gram-positive, which are used to screen for activity against pathogenic bacteria. The antibacterial spectrum and potency of a particular compound may be determined in a standard test system. The compounds have particularly high activity in vitro against strains of *Pseudomonas aeruginosa*.

The antibacterial properties of the compounds of the invention may also be demonstrated in vivo in conventional mouse protection tests.

Cephalosporin derivatives have generally been found to be relatively non-toxic to warm-blooded animals, and this generalisation holds true for the compounds of the present invention. Compounds representative of the present invention were administered to mice at doses in excess of those required to afford protection against bacterial infections, and no overt toxic symptoms or side effects attributable to the administered compounds were noted.

The following results were obtained for representative compounds on a standard in vitro test system using Isosensitest agar medium. The antibacterial activity is described in terms of the minimum inhibitory concentration (MIC) determined by the agar-dilution technique with an inoculum size of $10^4$ CFU/spot.

| ORGANISM | MIC ($\mu$l/ml) EXAMPLE | | | | |
|---|---|---|---|---|---|
|  | 1 | 2 | 6 | 7 | 8 |
| P. aeruginosa PU21 (A8101028) | 0.008 | 0.008 | 0.015 | 0.008 | 0.008 |
| Ent. cloacae P99 (A8401054) | 0.006 | 0.008 | 0.06 | 0.008 | 0.125 |
| Serr. marcesens (A8421003) | 0.008 | 0.008 | 0.008 | 0.008 | 0.06 |
| Pr. morganii (A8433001) | 0.008 | 0.125 | 0.008 | 0.06 | 0.25 |
| Kleb. oxytoca (A8395055) | 0.008 | 0.008 | 0.008 | 0.008 | 0.015 |
| E. coli DCO (A8341098) | 0.008 | 0.008 | 0.008 | 0.008 | 0.008 |
| St. aureus 147N (A8601052) | 16 | 32 | >16 | 32 * | 8 |
| S. dublin (A8369001) | 0.008 | 0.008 | 0.008 | 0.015 | 0.03 |
| Strep. pyogenes (A681018) | N/A | 1 | 2 | 0.03 | 0.06 |

In comparison, the Examples of U.S. Pat. No. 4,728,732, according to the test methods described in that patent, afforded MIC ($\mu$g/ml) of:

| Organism | MIC ($\mu$g/ml) |
|---|---|
| St. aureus ATCC29213 | 4–128 |
| E. cloacae ATCC13047 | 4–128 |
| E. coli ATCC25922 | 1–8 |
| K. pneumoniae KL-1 | 0.5–4 |
| P. aeruginosa ATCC27853 | 32–256 |
| S. marcesens ATCC13880 | 2–32 |

In the Examples, unless otherwise stated:
a) nuclear magnetic resonance (NMR) spectra were determined at 200 MHz in $d_6$-dimethylsulphoxide (DMSO)/$d_4$-acetic acid/d-trifluoroacetic acid as solvent using tetramethylsilane (TMS) as an internal standard. Spectra are expressed in delta values (parts per million) for protons relative to TMS using conventional abbreviations to described signal types.
b) chromatography was performed on HP20SS resin using methanol/water mixtures containing 1% trifluoroacetic acid (eluant A) or acetonitrile/water mixtures containing 1% acetic acid (eluant B) or methanol/water mixtures containing 1% acetic acid (eluant C)
c) DMSO represents dimethylsulphoxide
d) DMF represents dimethylformamide

EXAMPLE 1

7-[2-(2-Aminothiazol-4-yl)-2-((Z)-1-carboxy-1-methylethoxyimino)acetamido]-3-(5,6-dihydroxy-1,3-dioxoisoindol-2-ylmethyl)ceph-3-em-4-carboxylic acid To 7-[2-(2-aminothiazol-4-yl)-2-((Z)-1-carboxy-1-methylethoxyimino)acetamido]-3-(5,6-diphenylmethylenedioxy-1,3-dioxoisoindol-2-ylmethyl)ceph-3-em-4-carboxylic acid (70 mg) was added trifluoroacetic acid (4 ml) followed by water (two drops). The solution was stirred for 4 hours at ambient temperature. The solvent was removed by evaporation and the solid residue was diluted with dimethylformamide (3 ml) and subjected to column chromatography (eluant A) to afford the title compound (30 mg); NMR (DMSO-$d_6$/CD$_3$COOD/CF$_3$COOD) 1.5(2s,6H); 3.25(d,1H); 3.55(d,1H); 4.35(d,1H); 4.80(d,1H); 5.1(d,1H); 5.80(d,1H); 7.05(s,1H); 7.1(s,2H): M/S 647 (M+H)$^+$.

The starting material for the above reaction was obtained as follows:

a) To a solution of 3,4-dimethoxytoluene (15 g) and dichloromethylmethyl ether (34.5 g) in dichloromethane (200 ml), at 0° C., was added SnCl$_4$ (100 ml) and, subsequently, further dichloroethane (200 ml). The resultant suspension was stirred at 0° C. for 20 minutes and then stirred overnight at ambient temperature before being poured into 3N HCl (500 ml) at 0° C. Extraction into dichloromethane, drying of the organic phase and evaporation gave 4,5-dimethoxy-2-methylbenzaldehyde (15.2 g); NMR (CDCl$_3$) 2.6(s,3H); 3.90(s,3H); 3.94(s,3H); 6.68(s,1H); 7.3(s,1H); 10.2(s,1H).

b) To the aldehyde from a) (5.0 g) and potassium carbonate (5 g) in water (21 ml) at 80° C. was added, all at once, a solution of potassium permanganate (19 g) in water (170 ml). The solution was heated at 90°–95° C. for 1 hour, cooled, neutralised with 5N HCl (50 ml) and filtered through diatomaceous earth. The aqueous phase was concentrated, extracted into ethyl acetate; the organic phase was dried and evaporated to give 2-carboxy-4,5-dimethoxybenzoic acid (2.85 g); NMR (CDCl$_3$/DMSO-$d_6$) 3.95(s,6H); 7.5(s,2H); 11.2(broad s,2H).

c) The di-acid from b) (1.5 g) and acetic anhydride (6 g) were heated at reflux for 1 hour. The mixture was cooled and evaporated to provide dimethoxyphthalic anhydride (1.28 g); NMR (DMSO-$d_6$) 3.99(s,6H); 7.6(s,2H).

d) To the anhydride from c) (2.0 g) was added 28% ammonia solution (2.3 g) and the solution was taken to boiling-point, eliminating water in order to obtain a thick paste. This was cooled to give a brown solid which was finely ground. This solid was heated by a flame (without fusion) to give dimethoxyphthalimide (1.7 g); NMR (DMSO-$d_6$) 3.9(s,6H); 7.3(s,2H); 10.9(s,1H): M/S 225(M+NH$_3$+). The reaction was monitored by HPLC.

e) To the dimethoxyphthalimide from d) (3.1 g) were added BBr$_3$ (12 ml) and dichloromethane (30 ml). The suspension was stirred at ambient temperature until HPLC showed that starting-material had disappeared. Excess solvent was evaporated and the resultant solid cooled to 0° C. and treated with ice and then with water (80 ml). The mixture was stirred for 45 minutes at ambient temperature, water (40 ml) removed by evaporation and the residue purified by column chromatography (eluant A) to provide the corresponding dihydroxyphthalimide (2.13 g); NMR (DMSO-$d_6$) 7.1(s,2H); 10.25(broad s, 2H); 11.25(broad s, 1H).

f) A suspension of the dihydroxyphthalimide from e) (350 mg) in diphenyldichloromethane (4 g) was heated at 160° C. for 3 hours. The resultant solution was cooled and washed with petroleum ether (3×10 ml). The petrol phase separated to give a brown oil which was collected and triturated under diethyl ether (5 ml) to give as a chestnut brown solid, diphenylmethylenedioxyphthalimide (300 mg); NMR (DMSO-$d_6$) 7.5(m,12H); 11.05(s,1H). Cooling of the petrol phase afforded a second fraction of the phthalimide (250 mg).

g) To a suspension of sodium hydride (4 mg; 50%) (washed with tetrahydrofuran) was added, dropwise, a solution of phthalimide (f) (500 mg), in DMF (1.5 ml). The mixture was stirred for 1 hour at ambient temperature, cooled to 0° C. and ethyl chloroformate (180 μl) was added, dropwise. The resultant solution was stirred at 0° C. for 5 minutes, stirred at ambient temperature for 3 hours, cooled to 0° C. and water (5 ml) added with stirring. The solution was extracted with diethyl ether (150 ml). The ether phase was washed with water (3×20 ml), saturated NaCl (20 ml), dried, filtered and evaporated to give N-carboethoxy diphenylmethylenedioxyphthalimide (600 mg); NMR (CDCl$_3$) 1.40(t,3H); 4.45(q,2H); 7.25–7.75(m,12H).

h) To a solution of 7-[2-(2-aminothiazol-4-yl)-2-((Z)-1-carboxy-1-methylethoxyimino)acetamido]-3-em-4-carboxylic acid (143 mg) in DMSO (2 ml) was added triethylamine (62.4 mg) followed by the phthalimide from g) above (85.6 mg) in DMSO (1 ml). The solution was stirred at ambient temperature for 90 minutes, concentrated HCl (10 drops) added and after storage at 3° C. for 12 hours the solution was evaporated and purified by column chromatography (eluant B) to give 7-[2-(2-aminothiazol-4-yl)-2-((Z)-1-carboxy-1-methylethoxyimino)acetamido]-3-(5,6-diphenylmethylenedioxy-1,3-dioxo-isoindol-2-ylmethyl)ceph-3-em-4-carboxylic acid (70 mg); NMR (DMSO-$d_6$/CF$_3$COOD) 1.5(2s,6H); 3.3(d,1H); 3.6(d,1H); 4.4(d,1H); 4.90(d,1H); 5.1(d,1H); 5.80(d,1H); 7.05(s,1H); 7.25–7.75(m,12H).

The synthetic route is pictured in Scheme 1.

SCHEME I

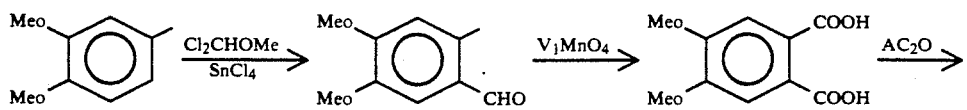

-continued
SCHEME I

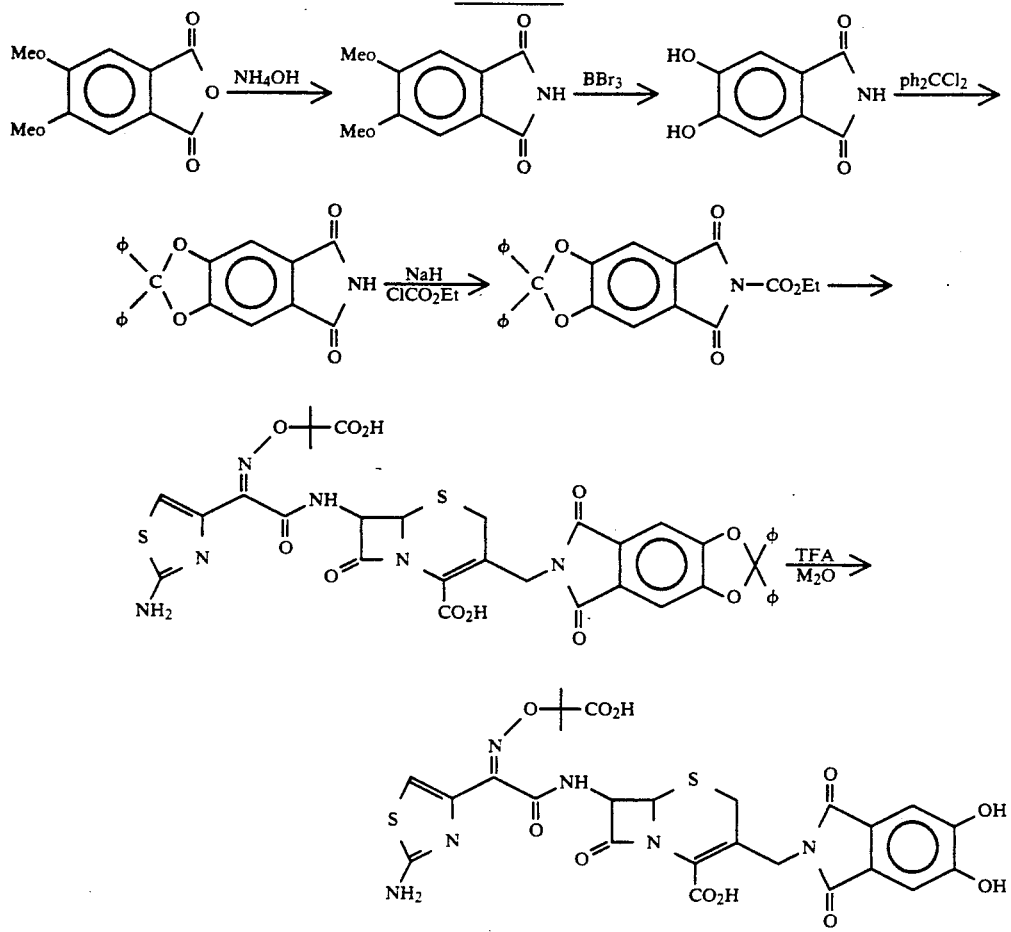

EXAMPLES 2-5

In a manner similar to that of Example 1 and Scheme 1, the following compounds were prepared.

EXAMPLE 2

2-Bromo-3,4-dimethoxytoluene was prepared by the bromination in acetic acid of vanillin, followed by

| Example | $R^1$ | $R^2$ | $R^3$ | $R^4$ | NMR DATA (DMSO-$d_6$/CF$_3$COOD/CD$_3$COOD) |
|---|---|---|---|---|---|
| 2 | Br | OH | OH | H | 1.5(2s, 6H); 3.25(d, 1H); 3.55(d, 1H); 4.35(d, 1H); 4.90(d, 1H); 5.1(d, 1H); 5.80(d, 1H); 7.05(s, 1H); 7.15(s, 1H). |
| 3 | Cl | OH | OH | Cl | 1.5(2s, 6H); 3.3(d, 1H); 3.6(d, 1H); 4.35(d, 1H); 4.9(d, 1H); 5.1(d, H); 5.8(d, 1H); 7.05(s, 1H). |
| 4 | OH | OH | H | H | 1.52(s, 6H); 3.35(d, 1H); 3.60(d, 1H); 4.35(d, 1H); 4.90(d, 1H); 5.15(d, 1H); 5.80(d, 1H); 7-7.25(m, 3H). |
| 5 | OH | OH | Br | H | 1.53(2s, 6H); 3.3(d, 1H); 3.6(d, 1H); 4.4(d, 1H); 4.95(d, 1H); 5.15(d, 1H); 5.8(d, 1H); 7.05(s, 1H); 7.45(s, 1H). |

Footnotes methylation (($CH_3)_2SO_4$/$K_2CO_3$) to give the dimethoxy compound and subsequent treatment with hydrazine at an elevated temperature to reduce the aldehyde. Steps analogous to Example 1a)–h) were subsequently performed.

EXAMPLE 3

4,5-Dihydroxyphthalimide (Example 1e) was heated for 6 hours with N-chlorosuccinimide in acetic acid in the presence of toluene sulphonic acid to give 3,6-dichloro-4,5-dihydroxyphthalimide which was subsequently treated in a manner similar to Example 1f)–h).

EXAMPLE 4

2,3-Dimethoxytoluene was taken through a reaction sequence analogous to that of Example 1.

EXAMPLE 5

3,4-Dihydroxyphthalimide (Example 4e) was heated with bromine in acetic acid for about 6 hours to give 5-bromo-3,4-dihydroxyphthalimide which was subsequently treated in a manner similar to Example 1f)–h).

Example 6

7-[2-(2-Aminothiazol-4-yl)-2-((Z)-1-carboxy-1-methylethoxyimino)acetamido]-3-(5,6-dihydroxy-3-oxo-1,2-benzisothiazol-2(3H)-ylmethyl)ceph-3-em-4-carboxylic acid $-S^3-,S^3-$dioxide.

A solution of 7-[2-(2-aminothiazol-4-yl)-2-((Z)-1-t-butoxycarbonyl-1-methylethoxyimino)acetamido]-3-(5,6-dihydroxy-3-oxo-1,2-benzisothiazol-2(3H)-ylmethyl)ceph-3-em-4-carboxylic acid, t-butylester, $S^3,S^3-$dioxide (55 mg) in dichloromethane (10 ml) and trifluoroacetic acid (1 ml) was stirred at ambient temperature for 2 hours and evaporated under reduced pressure to give a brown oil which was purified by chromatography on Dynamax $C_{18}$ reverse phase column. Freeze-drying afforded the title compound (3 mg) as a white solid; NMR (DMSO-$d_6$) 1.53(s,3H); 1.56(s,3H); 3.4(d,1H); 3.6(d,1H); 4.65(d,1H); 4.95(d,1H); 5.15(d,1H); 5.85(q,1H); 7.05(s,1H); 7.28(s,1H); 7.35(s,1H); 9.6(d,1H); M/S +ve FAB (M+H)+ 683.

The starting-material was obtained as follows:
a) To a solution of t-butylamine (15.8 ml) in chloroform (25 ml), at ice-bath temperature, was added over 1 hour a solution of 3,4-dimethoxybenzene sulphonyl chloride (11.83 g) in chloroform (75 ml). The solution was allowed to warm to ambient temperature, stirred for 2 hours and then stirred under reflux for a further hour. The mixture was cooled, washed with 3N HCl (2×70 ml), water (100 ml), dried (MgSO$_4$), filtered and evaporated under reduced pressure to give N-(t-butyl-3,4-dimethoxybenzenesulphonamide (12.77 g); NMR (CDCl$_3$) 1.23(s,9H); 3.92(s,3H); 3.94(s,3H); 4.50(broad s,1H); 6.91(d,1H); 7.37(d,1H); 7.50(dd,1H); M/S 274 (M+H)+.
b) sec-Butyl lithium in cyclohexane (0.92M; 54 ml) was added, under argon atmosphere, to a cooled solution (−35° C.) of compound from a) above (0.02M; 5.46 g) in tetrahydrofuran (140 ml). The mixture was stirred for 10 minutes at −35° C. and for 1½ hours at ambient temperature. Carbon dioxide was passed through the solution for 30 minutes, water (70 ml) was added followed by concentrated HCl (13 ml) with cooling. Tetrahydrofuran was removed by evaporation under reduced pressure and the aqueous residue was extracted into chloroform (2×100 ml). The chloroform layer was dried (MgSO$_4$), filtered and evaporated to give a solid. This was purified by column chromatography using silica ART 9385 (Merck) (eluant: acetic acid (0.5)/ethanol(0.25)/dichloromethane (9.25)) to give, after recrystallisation N-t-butyl-6-carboxy-3,4-dimethoxybenzenesulphonamide (0.7 g); NMR (CDCl$_3$) 1.24(s,9H); 3.95(s,3H); 3.97(s,3H); 6.62(br s,1H); 7.47(s,1H); 7.62(s,1H); M/S 318 (M+H)+.
c) A suspension of the product from b) above (4.28 g) in polyphosphoric acid (143 ml) was heated on a steam bath for 20 minutes whilst the mixture was stirred manually with a spatula. The resultant hot, yellow syrup was poured on to ice (713 g) and stirred vigorously for 15 minutes. The precipitate was collected by filtration, washed well with water and dried (at 60° C.) under vacuum to give 5,6-dimethoxy-1,2-benzisothiazolin-3-one-1,1-dioxide (1.7 g); NMR (DMSO-$d_6$) 3.93(s,3H); 3.95(s,3H); 7.41(s,1H); 7.71(s,1H); M/S 261(M+NH$_4$)+.
d) Boron tribromide (6.95 ml; 4 equivalents) was added to a suspension of compound from c) above (4.4 g) in dichloromethane (75 ml) under argon at −40° C. The reaction was allowed to warm to ambient temperature over 1½ hours. The mixture was carefully added to ice and left to melt. The reaction was filtered to give a solid which was recrystallised from water to give, as a solid, 5,6-dihydroxy-1,2-benzisothiazolin-3-one-1,1-dioxide (5,6-dihydroxysaccharin) (0.55 g); NMR (DMSO-$d_6$) 10.85(br,1H); 10.55(br,1H); 7.25(s,1H); 7.15(s,1H); MS CI(NH$_3$) (M+H)+ 216. Melting point=332°–333° C. (dec).
e) To a suspension of sodium hydride (0.15 g) in DMF (2 ml) was added 5,6-dihydroxysaccharin (0.15 g). The mixture was stirred for 40 minutes. A solution of 7-[2-(2-aminothiazol-4-yl)-2-((Z)-1-t-butoxycarbonyl-1-methylethoxyimino)acetamido]-3-iodomethyl-ceph-3-em-4-carboxylic acid, t-butyl ester (0.15 g) in DMF (2 ml) was added and the mixture was stirred for a further four hours, diluted with ethyl acetate and washed thoroughly with water. The organic phase was dried (MgSO$_4$) and evaporated to give a foam which was purified by chromatography on HP20SS resin (eluant methanol/water) to give 7-[2-(2-aminothiazol-4-yl)-2-((Z)-1-carboxy-1-methylethoxyimino)acetamido]-3-(5,6-dihydroxy-3-oxo-1,2-benzisothiazol-2(3H)-ylmethyl)ceph-3-em-4-carboxylic acid $-S^3,S^3-$dioxide (35 mg); NMR (DMSO-$d_6$) 1.43(s,9H); 1.63(s,15H); 3.45(d,1H); 3.65(d,1H); 4.66(d,1H); 4.95(d,1H); 5.22(d,1H); 5.9(q,1H); 7.1(s,1H); 7.37(s,1H); 7.4(s,1H); 9.6(d,1H); M/S +ve FAB (M+H)+ 795.

EXAMPLE 7

7-[2-(2-Aminothiazol-4-yl)-2-((Z)-1-carboxy-1-methylethoxyimino)acetamido]-3-(6,7-dihydroxy-3-oxo-tetrahydroisoquinolin-2-ylmethyl)ceph-3-em-4-carboxylic acid To 7-[2-(2-aminothiazol-4-yl)-2-((Z)-1-carboxy-1-methylethoxyimino)acetamido]-3-(4,5-dihydroxy-2-methoxycarbonylmethylbenzylaminomethyl)ceph-3-em-4-carboxylic acid (800 mg) in acetonitrile (5 ml) and water (5 ml), at 0° C., was added triethylamine (260 μl). The mixture was stirred, at ambient temperature, for 90 minutes and evaporated under reduced pressure. The residue was dissolved in water (25 ml) containing acetic acid (a few drops) and sodium acetate, filtered and purified by chromatography (HPLC; Dynamax column) using 17.5% acetonitrile/water. Freeze-drying afforded the title compound (58 mg); NMR (DMSO-$d_6$/$CF_3COOH$) 1.49(s,3H); 1.52(s,3H); 3.35(dd,2H); 3.4(s,3H); 4.3(m,2H); 4.5(dd,2H); 5.18(d,1H); 5.85(dd,1H); 6.58(d,1H); 6.62(s,1H); 9.7(d,1H): FAB M/S (M-H)⁻645.

The starting material for the above reaction was obtained as follows:

a) 3,4-Dimethoxyphenylacetic acid (20 g) and concentrated sulphuric acid (1 ml) in methanol (70 ml) were stirred at reflux for 16 hours. Methanol was removed by evaporation and the residue poured into cold water (250 ml) with stirring). Extraction into ethyl acetate (2×100 ml), washing with saturated $NaHCO_3$ (100 ml) and brine (100 ml) followed by evaporation under reduced pressure gave, as an orange oil, 3,4-dimethoxyphenylacetic acid methyl ester (18 g); NMR (DMSO-$d_6$) 3.57(s,2H); 3.62(s,3H); 3.73(s,6H); 6.75(dd,1H); 6.88(s,1H); 6.89(d,1H).

b) To the product from a) above (14.25 g) in dichloromethane (30 ml), at 0° C., was added $SnCl_4$ (15.6 ml). Dichloromethylmethyl ether (10.7 ml) in dichloromethane (30 ml) was added over a period of 10 minutes such that the temperature did not rise above 15° C. A further portion of dichloromethylmethyl ether (2.5 ml) was added to the cooled reaction mixture after 1 hour. After a further 30 minutes, at 0° C., the reaction mixture was poured into water and extracted into ethyl acetate. The organic phase was washed with saturated $NaHCO_3$, dried ($MgSO_4$) and evaporated under reduced pressure to give, after crystallisation from toluene, 3,4-dimethoxy-6-(methoxycarbonylmethyl)benzaldehyde; NMR (DMSO-$d_6$) 3.60(s,3H); 3.84(s,6H); 4.05(s,2H); 7.02(s,1H); 7.43(s,1H); 9.98(s,1H).

c) The product from b) above (1.5 g) in dichloromethane (5 ml) was added, with stirring, to boron tribromide (1.8 ml) in dichloromethane at −78° C. The reaction mixture was allowed to warm to ambient, stirred for 150 minutes and added to methanol at 0° C. The resultant solution was stirred for 16 hours, solvent was removed by evaporation and the residue purified by chromatography on a HP20SS column using aqueous acetonitrile as eluant to provide 3,4-dihydroxy-6-methoxycarbonylmethyl)benzaldehyde (1.2 g); NMR (DMSO-$d_6$) 3.59(s,3H); 3.9(s,2H); 6.71(s,1H); 7.23(s,1H); 9.82(s,1H).

d) The product from c) (210 mg) in DMF (1 ml) was added, at 0° C., to a suspension of 7-[2-(2-aminothiazol-4-yl)-2-((Z)-1-carboxy-1-methylethoxyimino)acetamido]-3-aminomethylceph-3-em-4-carboxylic acid (484 mg) in methanol/water (9:1 ratio; 7 ml) under an argon atmosphere. Sodium cyanoborohydride (63 mg) was added, reaction mixture was stirred for 3 hours at ambient temperature and solvent evaporated under reduced pressure to give a residue. This was dissolved in 10% aqueous acetonitrile (30 ml) containing acetic acid and sodium acetate and purified by preparative HPLC chromatography (Dynamax) using acetonitrile/water containing 0.1% trifluoroacetic acid as eluant to a carboxy-1-methylethoxyimino)acetamido]-3-(4,5-dihydroxy-2-(methoxycarbonylmethyl)benzylaminomethyl)ceph-3-em-4-carboxylic acid (50 mg); NMR (DMSO-$d_6$/$CF_3COOH$) 1.50(s,3H); 1.53(s,3H); 3.63(s,3H); 3.7(m,2H); 3.92(m,2H); 4.1(m,2H); 5.22(d,1H); 5.9(dd,1H); 6.72(s,1H); 6.95(s,1H); 7.1(s,1H); 8.3(s,1H); 9.1(s,1H); 9.62(d,2H): FAB M/S (M-H)⁻678.

EXAMPLE 8

7-[2-(2-Aminothiazol-4-yl)-2-((Z)-1-carboxy-1-methylethoxyimino)acetamido]-3-(8-bromo-6,7-dihydroxy-3-oxo-tetrahydroisoquinolin-2-ylmethyl)ceph-3-em-4-carboxylic acid To 7-[2-(2-aminothiazol-4-yl)-2-((Z)-1-carboxy-1-methylethoxyimino)acetamido]-3-(3-bromo-4,5-dihydroxy-2-methoxycarbonylmethylbenzylaminomethyl)-ceph-3-em-4-carboxylic acid (378 mg) in acetonitrile (3.5 ml) and water (3.5 ml), at 0° C., was added triethylamine (108 μl). The mixture was stirred, at ambient temperature, for 60 minutes, stored at 0° C. overnight and evaporated under reduced pressure. The residue was dissolved in water (20 ml) containing acetic acid (a few drops) and sodium acetate, filtered and purified by chromatography (preparative HPLC; Dynamax column) using 20% acetonitrile/water. Freeze-drying afforded the title compound (86 mg); NMR (DMSO-$d_6$/$CD_3COOD$) 1.45(s,3H); 1.46(s,3H); 3.6(s,2H); 3.65(m,2H); 3.9(m,2H); 4.1(m,2H); 5.15(d,1H); 5.9(d,1H); 6.75(s,1H); 6.95(s,1H): FAB M/S (M-H)⁻727.

The starting material for the above reaction was obtained as follows:

a) Bromine (192 μl) was added to a suspension of 3,4-dihydroxy-6-(methoxycarbonylmethyl)benzaldehyde (0.79 g) in acetic acid (15 ml). The reaction mixture was stirred at ambient temperature for 5–6 hours, diluted with water (30 ml) and extracted into ethyl acetate (200 ml). The organic phase was washed with $NaHCO_3$, water (100 ml) and brine, dried and evaporated under reduced pressure to give a brown solid. This was purified by chromatography using aqueous acetonitrile mixtures to give 3-bromo-4,5-dihydroxy-2-(methoxycarbonylmethyl)benzaldehyde (300 mg); NMR (DMSO-$d_6$) 3.61(s,3H); 4.24(s,2H); 7.24(s,1H); 9.8(s,1H): CI M/S (M+H)⁺ 291.

b) The product from a) above (300 mg) in DMF (1 ml) was added, at 0° C., to a suspension of 7-[2-(2-aminothiazol-4-yl)-2-((Z)-1-carboxy-1'-methylethoxyimino)acetamido]-3-aminomethylceph-3-em-4-carboxylic acid (503 mg) in methanol/water (9:1 ratio: 5 ml) under an argon atmosphere. Further DMF (2 ml) was added in order to form a solution. After 5 minutes, sodium cyanoborohydride (66 mg) was added and the reaction mixture was stirred at ambient temperature for 4½ hours. The solvent was evaporated under reduced pressure and the residue was purified by chromatography using aqueous acetonitrile mixtures to give 7-[2-(2-aminothiazol-4-yl)-2-((Z)-1-carboxy-1-methylethoxyimino)acetamido]-3-(3-bromo-4,5-dihydroxy-2'-(methoxycarbonylmethyl)benzylaminomethyl)-ceph-3-em-4-carboxylic acid (100 mg); NMR (DMSO-$d_6$/$CD_3COOD$) 1.45(s,3H); 1.46(s,3H); 3.35(dd,2H); 3.45(s,2H); 4.3(dd,2H); 4.45(dd,2H); 5.15(d,1H); 5.85(d,1H); 6.6(s,1H); 6.8(s,1H); FAB M/S (M−H)⁻ 759.

EXAMPLE 9

7-[2-(2-Aminothiazol-4-yl)-2-((Z)-1-carboxy-1-methylethoxyimino)acetamido]-3-(5,6-diphenylmethylenedioxy-4,7-dibromo-1,3-dioxoisoindol-2-ylmethyl)ceph-3-em-4-carboxylic acid To 7-[2-(2-aminothiazol-4-yl)-2-((Z)-1-carboxy-1-methylethoxyimino)acetamido]-3-aminomethylceph-3-em-4-carboxylic acid (75.8 mg) in DMSO (1.8 ml) was added triethylamine (47.5 mg) in DMSO (2.5 ml) followed by N-carboethoxy-5,6-diphenylmethylenedioxy-4,7-dibromo-1,3-dioxoisoindole (90 mg). The solution was stirred for 3 hours 30 minutes at room temperature, concentrated HCl (6 drops) added and after storage at $-20°$ C. for 12 hours the solution was purified by column chromatography (eluant C) to afford the title compound (60 mg); NMR (DMSO-$d_6$/CF$_3$COOD) 1.55(s,6H); 3.3(d,1H); 3.65(d,1H); 4.4(d,1H); 4.9(d,1H); 5.1(d,1H); 5.85(d,1H); 7.05(s,1H); 7.5(s,10H).

The starting material for the above reaction was obtained as follows:

a) To a solution of dihydroxyphthalimide (as prepared in 1e) (44 mg) in acetic acid (2 ml) was added a solution of bromine (500 mg) in acetic acid (3 ml). The solution was stirred for 16 hours at room temperature. After filtration, the filtrate was washed with ether to give 5,6-dihydroxy-4,7-dibromo-1,3-dioxo isoindole (40 mg) as a beige solid.

b) A solution of the isoindole from (a) above (400 mg) in dichlorodiphenylmethane (618 mg) was heated at 160° C. for 4 hours. After cooling, petroleum ether was added and the suspension was filtered. The filtrate was washed with petroleum ether to give as a beige solid 5,6-diphenylmethylenedioxy-4,7-dibromo-1,3-dioxo isoindole (448 mg); NMR (DMSO-$d_6$): 7.5(s,10H); 11.2(s,1H).

c) To a suspension of NaH (8 mg; 50% in oil) in dimethyl formamide (1 ml) was added a solution of the isoindole from (b) above (80 mg) in dimethyl formamide (1 ml). After stirring for 1 hour 30 minutes at room temperature, the solution was cooled to 0° C. and freshly distilled ethylchloroformate was added (22.4 mg). Stirring was maintained for 5 minutes at 0° C. and for 2 hours at room temperature. After cooling at 0° C. water (3 ml) was added and stirring continued for 15 minutes at room temperature.

After extraction with ether, the organic layer was washed with brine, dried with MgSO$_4$ and evaporated to give as a beige solid, N-carboethoxy-5,6-diphenylmethylenedioxy-4,7-dibromo-1,3-dioxo isoindole (90 mg);

NMR (DMSO-$d_6$): 1.32(t,3H); 4.35(q,2H); 7.5(s,10H).

We claim:

1. A compound of the formula

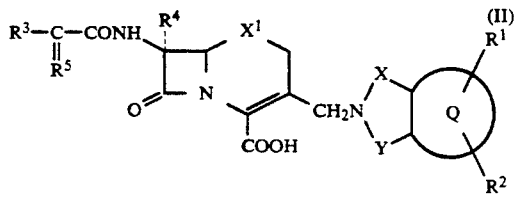

(II)

and salts and esters thereof wherein

X is —CO— or —COCH$_2$—;

Y is —CO— or —CH$_2$—;

Q is a benzene, pyridine or naphthalene ring system;

$R^1$ is hydroxy or a group of the formula O—M wherein M is a moiety and the O—M bond is cleavable in vivo;

$R^2$ is ortho to $R^1$ and is hydroxy or a group of the formula O—M wherein

M is a moiety and the O—M bond is cleavable in vivo;

and wherein Q is optionally substituted by $C_{1-6}$alkyl, halo, hydroxy, cyano, trifluoromethyl, nitro, amino, $C_{1-6}$alkylamino, di-$C_{1-6}$alkylamino, $C_{1-6}$alkanoyl, $C_{1-6}$alkoxy, $C_{1-6}$alkylthio, $C_{1-6}$alkanoyloxy, carbamoyl, $C_{1-6}$alkylcarbamoyl, di-$C_{1-6}$alkylcarbamoyl, carboxy, carboxy$C_{1-6}$alkyl, $C_{1-6}$alkoxycarbonyl, hydroxy$C_{1-6}$alkyl, $C_{1-6}$alkanoylamino or $C_{1-6}$alkoxycarbonyl$C_{1-6}$alkyl $X^1$ is sulphur or sulphinyl;

$R^4$ is hydrogen, methoxy or formamido; and $R^3$ is 2-aminothiazol-4-yl or 2-aminooxazol-4-yl each optionally substituted in the 5-position by fluorine, chlorine or bromine, or is 5-aminoisothiazol-3-yl, 5-amino-1,2,4-thiadiazol-3-yl, 3-aminopyrazol-5-yl, 3-aminopyrazol-4-yl, 2-aminopyrimidin-5-yl, 2-aminopyrid-6-yl, 4-aminopyrimidin-2-yl, 2-amino-1,3,4-thiadiazol-5-yl or 5-amino-1-methyl-1,2,4-triazol-3-yl;

$R^5$ is a group of the formula =N.O.$R^6$ (having the syn configuration about the double bond) wherein $R^6$ is hydrogen, (1-6C)-alkyl, (3-8C)cycloalkyl, (1-3C)alkyl(3-6C)cycloalkyl, (3-6C)-cycloalkyl(1-3C)alkyl, (3-6C)alkenyl, optionally substituted by carboxy, (5-8C)cycloalkenyl, (3-6C)alkynyl, (2-5C)alkylcarbamoyl, phenylcarbamoyl, benzylcarbamoyl, (1-4C)alkylcarbamoyl(1-4C)alkyl, di(-1-4C)alkylcarbamoyl(1-4C)alkyl, (1-4C)haloalkylcarbamoyl(1-4C)-alkyl, (1-3C)haloalkyl, (2-6C)hydroxyalkyl, (1-4C)alkoxy(2-4C)alkyl, (1-4C)alkylthio(2-4C)alkyl, (1-4C)alkanesulphinyl(1-4C)alkyl, (1-4C)-alkanesulphonyl(1-4C)alkyl, (2-6C)aminoalkyl, (1-4C)alkylamino(1-6C)-alkyl, (2-8C)dialkylamino(2-6C)alkyl, (1-5C)cyanoalkyl, 3-amino-3-carboxypropyl, 2-(amidinothio)ethyl, 2-(N-aminoamidinothio)ethyl, tetrahydropyran-2-yl, thietan-3-yl, 2-oxopyrrolidinyl, or 2-oxotetrahydrofuranyl, or $R^6$ is of the formula (III):

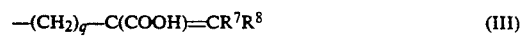

wherein q is one or two and $R^7$ and $R^8$ are independently hydrogen or $C_{1-4}$alkyl; or $R^6$ is of the formula (IV):

wherein r is 0–3, $R^9$ is hydrogen, (1-3C)alkyl or methylthio, $R^{10}$ is hydrogen, (1-3C)alkyl, (3-7C)cycloalkyl, cyano, carboxy, (2-5C)carboxyalkyl or methanesulphonylamino, or $R^9$ and $R^{10}$ are joined to form, together with the carbon to which they are attached, a (3-7C)carbocyclic ring, and $R^{11}$ is hydroxy, amino, (1-4C)alkoxy, (1-4C) alkylamino or of the formula NHOR$^{12}$ in which $R^{12}$ is hydrogen or (1-4C)alkyl;

or $R^5$ may be of the formula =CH.$R^{13}$ wherein $R^{13}$ is hydrogen, halogen, (1-6C)alkyl, (3-7C)cycloalkyl, (2-6C)alkenyl, (3-7C)cycloalkenyl, phenyl or benzyl;

or a pharmaceutically acceptable salt threof.

2. A compound according to claim 1 wherein X is —COCH$_2$— and Y is —CH$_2$—.

3. A compound according to claim 1 wherein X is —CO— and Y is —CO—.

4. A compound according to claim 1 wherein Q is a benzene ring system.

5. A compound according to claim 1 wherein Q is optionally substituted by bromo, chloro, carboxy, carboxymethyl and hydroxy.

6. A compound according to claim 1 wherein R$^4$ is hydrogen and X$^1$ is sulphur;
or a pharmaceutically acceptable salt thereof.

7. A compound according to claim 1 wherein R$^3$ is 2-aminothiazol-4-yl or 2-aminooxazol-4-yl, R$^5$ is of the formula =N.O.R$^6$ (having the syn configuration about the double bond) wherein R$^6$ is methyl, ethyl, 1-carboxycyclobutyl, 1-carboxycyclopentyl, or 2-carboxyprop-2-yl, or R$^5$ is of the formula =CH.R$^{13}$ wherein R$^{13}$ is hydrogen, methyl, ethyl or chlorine; or a pharmaceutically acceptable salt thereof.

8. A compound according to claim 1 which is
7-[2-(2-aminothiazol-4-yl)-2-((Z)-1-carboxy-1-methylethoxyimino)acetamido]-3-(5,6-dihydroxy-1,3-dioxo-isoindol-2-ylmethyl)-ceph-3-em-4-carboxylic acid,
7-[2-(2-aminothiazol-4-yl)-2-((Z)-1-carboxy-1-methylethoxyimino)acetamido]-3-(5,6-dihydroxy-4-bromo-1,3-dioxo-isoindol-2-ylmethyl)-ceph-3-em-4-carboxylic acid, 7-[2-(2-aminothiazol-4-yl)-2-((Z)-1-carboxy-1-methylethoxyimino)acetamido]-3-(5,6-dihydroxy-4,7-dichloro-1,3-dioxo-isoindol-2-ylmethyl)-ceph-3-em-4-carboxylic acid, 7-[2-(2-aminothiazol-4-yl)-2-((Z)-1-carboxy-1-methylethoxyimino)acetamido]-3-(4,5-dihydroxy-1,3-dioxo-isoindol-2-ylmethyl)ceph-3-em-4-carboxylic acid, 7-[2-(2-aminothiazol-4-yl)-2-((Z)-1-carboxy-1-methylethoxyimino)acetamido]-3-(6-bromo-4,5-dihydroxy-1,3-dioxo-isoindol-2-ylmethyl)-ceph-3-em-4-carboxylic acid, 7-[2-(2-aminothiazol-4-yl)-2-((Z)-1-carboxy-1-methylethoxyimino)acetamido]-3-(5,6-dihydroxy-3-oxo-1,2-benzisothiazol-2(3H)-ylmethyl)-ceph-3-em-4-carboxylic acid-S$^3$, S$^3$-dioxide, 7-[2-(2-aminothiazol-4-yl)-2-((Z)-1-carboxy-1-methylethoxyimino)acetamido]-3-(6,7-dihydroxy-3-oxo-tetrahydroisoquinolin-2-ylmethyl)-ceph-3-em-4-carboxylic acid, 7-[2-(2-aminothiazol-4-yl)-2-((Z)-1-carboxy-1-methylethoxyimino)acetamido]-3-(8-bromo-6,7-dihydroxy-3-oxo-tetrahydroisoquinolin-2-ylmethyl)-ceph-3-em-4-carboxylic acid; or a pharmaceutically acceptable salt thereof.

9. An antibacterial pharmaceutical composition which comprises an antibacterial compound according to claim 1 and a pharmaceutically acceptable carrier.

10. A method of treating an infection comprising administering to a patient in need of such treatment an antibacterially effective amount of said compound according to claim 1, under conditions such that said treatment is effected.

* * * * *